(12) United States Patent
Yamano et al.

(10) Patent No.: US 9,175,831 B2
(45) Date of Patent: Nov. 3, 2015

(54) ILLUMINATION APERTURE DIAPHRAGM

(75) Inventors: Shiro Yamano, Sagamihara (JP); Takayuki Sato, Nankoku (JP)

(73) Assignee: YAMANO OPTICAL CO., LTD., Kanagawa (JP)

( * ) Notice: Subject to any disclaimer, the term of this patent is extended or adjusted under 35 U.S.C. 154(b) by 200 days.

(21) Appl. No.: 13/980,625

(22) PCT Filed: Dec. 22, 2011

(86) PCT No.: PCT/JP2011/079901
§ 371 (c)(1),
(2), (4) Date: Jul. 19, 2013

(87) PCT Pub. No.: WO2012/098806
PCT Pub. Date: Jul. 26, 2012

(65) Prior Publication Data
US 2013/0306880 A1 Nov. 21, 2013

(30) Foreign Application Priority Data

Jan. 20, 2011 (JP) .................................. 2011-010056

(51) Int. Cl.
*A61B 1/06* (2006.01)
*G01N 21/64* (2006.01)
(Continued)

(52) U.S. Cl.
CPC ................ *F21V 13/02* (2013.01); *A61B 1/043* (2013.01); *A61B 1/0638* (2013.01); *A61B 1/0646* (2013.01); *A61B 1/0669* (2013.01); *F21V 9/08* (2013.01); *G01N 21/64* (2013.01); *G02B 5/005* (2013.01); *G02B 23/2461* (2013.01); *G03B 9/02* (2013.01); *G03B 15/14* (2013.01)

(58) Field of Classification Search
CPC .... A61B 1/043; A61B 1/0638; A61B 1/0646; A61B 1/0669; G01N 21/64
See application file for complete search history.

(56) References Cited

U.S. PATENT DOCUMENTS 6,293,911 B1   9/2001  Imaizumi et al.
2004/0135921 A1  7/2004  Murata et al.
(Continued)

FOREIGN PATENT DOCUMENTS

JP    10-151104 A    6/1998
JP    10-201707      8/1998
(Continued)

OTHER PUBLICATIONS

International Search Report; International Application No. PCT/JP2011/079901, Mar. 13, 2012.
(Continued)

*Primary Examiner* — Mark R Gaworecki
(74) *Attorney, Agent, or Firm* — Oliff PLC

(57) ABSTRACT

An illumination aperture diaphragm 100A for a light source device for supplying illumination light in an endoscopic device to simultaneously observe a subject image formed by reflected illumination light in the visible light region and a fluorescence image from a fluorescent substance in a subject has a filter region 1 formed in a flat plate-like base material 3 and an aperture region 2 formed inside the filter region 1. The filter region 1 transmits light in the wavelength region of excitation light for allowing the subject to emit fluorescent light and reduces or blocks the transmission of the light in the visible light region that forms the subject image. An illumination aperture diaphragm 200A may include a plurality of diaphragm blade members 20A.

14 Claims, 10 Drawing Sheets

(51) Int. Cl.
*F21V 13/02* (2006.01)
*G02B 5/00* (2006.01)
*G03B 9/02* (2006.01)
*A61B 1/04* (2006.01)
*G03B 15/14* (2006.01)
*G02B 23/24* (2006.01)
*F21V 9/08* (2006.01)

(56) References Cited

U.S. PATENT DOCUMENTS

2004/0186351 A1 9/2004 Imaizumi et al.
2005/0226611 A1 10/2005 Kawaguchi
2008/0249368 A1 10/2008 Takei

FOREIGN PATENT DOCUMENTS

| JP | 2001-078205 | | 3/2001 |
| JP | 2002-369223 | A | 12/2002 |
| JP | 2004-205557 | A | 7/2004 |
| JP | 2004-205951 | | 7/2004 |
| JP | 3713347 | B2 | 11/2005 |
| JP | 2008-188196 | | 8/2008 |
| JP | 2008-259591 | A | 10/2008 |
| JP | 2009-067352 | | 4/2009 |
| WO | WO 2011/007461 | A1 | 1/2011 |

OTHER PUBLICATIONS

Notification of Transmittal of Translation of the International Preliminary Report on Patentability and Written Opinion mailed Aug. 1, 2013 in International Application No. PCT/JP2011/079901; International Filing Date: Dec. 22, 2011.
Notification Concerning Transmittal of the International Preliminary Report on Patentability mailed Aug. 1, 2013 in International Application No. PCT/JP2011/079901; International Filing Date: Dec. 22, 2011.
Mar. 30, 2015 Office Action issued in Chinese Application No. 201180065496.5.
Jul. 30, 2015 Search Report issued in European Patent Application No. 11856442.6.
US 6,692,429, 02/2004, Imaizumi et al. (withdrawn)

(a)

100A (b)

(CROSS-SECTIONAL VIEW TAKEN ALONG A-A)

(a)

100B (b)

(CROSS-SECTIONAL VIEW TAKEN ALONG A-A)

(a)

100C (b)

(CROSS-SECTIONAL VIEW TAKEN ALONG A-A)

(a)

100D (b)

(CROSS-SECTIONAL VIEW TAKEN ALONG A-A)

(a)

(CROSS-SECTIONAL VIEW TAKEN ALONG A-A)

(b)

(CROSS-SECTIONAL VIEW TAKEN ALONG A-A)

(c)

(CROSS-SECTIONAL VIEW TAKEN ALONG A-A)

20A

20B

20C (a)

(b)

(CROSS-SECTIONAL VIEW TAKEN ALONG A-A)

ILLUMINATION APERTURE DIAPHRAGM

RELATED APPLICATIONS

This application is a U.S. national phase application of International Application No. PCT/JP2011/079901 filed Dec. 22, 2011 claiming priority of Japanese Patent Application No. 2011-010056 filed Jan. 20, 2011.

FIELD OF INVENTION

The present invention relates to an illumination aperture diaphragm for simultaneously irradiating a subject with illumination light for observing a visible subject image and excitation light for observing a fluorescent subject image in an appropriate ratio of quantity of light.

BACKGROUND ART

In a medical field, there have been available a photodynamic diagnosis (PDD) and a photodynamic therapy (PDT). The PDD is a diagnosis by making use of the property of a light-sensitive substance that is distinctively accumulated in tumor bearing tissue and emits fluorescent light when being irradiated with excitation light. In the diagnosis, the light-sensitive substance is given in advance to a living body, and then the tumor bearing tissue is observed by the fluorescent light emitted therefrom. On the other hand, the PDT is a therapy for destroying the tumor bearing tissue using singlet oxygen that is produced by the light-sensitive substance being excited.

In the PDD and PDT, the fluorescent light emitted from the light-sensitive substance in the tumor bearing tissue is required to be imaged and observed with high accuracy under intense illumination light, for example, from shadowless lamps in the operating room. The fluorescent light emitted from the light-sensitive substance is very weak when compared with the illumination light, thus raising the problem that the fluorescence image is buried in the subject image formed by the illumination light.

On the other hand, in recent years, attention has been focused on the method in which the indocyanine green (ICG) is given to the living body as a light contrast agent and excited by being irradiated with excitation light, so that a near-infrared fluorescence image emitted by the ICG is taken and observed in conjunction with the subject image to make a diagnosis. Hemoglobin absorbs light of wavelength shorter than 600 nm and water absorbs light of wavelength longer than 900 nm. On the other hand, the excitation wavelength of the ICG and the wavelength of the fluorescent light emitted by the ICG lie in a wavelength band from 600 to 900 nm in which no absorption by hemoglobin and water takes place. Thus, use of the ICG makes it possible to observe the inside of the living body. However, this method also has the problem that the fluorescence image is buried in the subject image.

To solve such problems, it was suggested that when the subject image including the fluorescent light in the infrared region was separated into RGB components and then the RGB components were re-combined to form a color image, the subject image was separated so as to be richer in the R component, thereby emphasizing the portion being observed that was formed by the weak fluorescent light (Patent Literature 1). However, in this method, since not only the fluorescent light in the infrared region but also the R component light forming the subject image are emphasized at the same time, it is difficult to accurately observe the portion emitting the fluorescent light in the subject image. There is also a problem that a filter for separating the subject image into the RGB components and a mechanism for driving the same are required, leading to an increase in the complexity of the whole system configuration.

It was also suggested that to allow excitation light to be cut and light in the infrared band and the visible light band to be transmitted and received in an imaging device for simultaneously taking a fluorescence image in the infrared band and a subject image in the visible light band, an optical filter having different transmittances for the infrared band and the visible light band should be used to balance between the infrared light image and the visible light image (Patent Literature 2). However, it is difficult to obtain an optical filter which has well-balanced transmittances for the infrared band and the visible light band when the light in the infrared band for forming the fluorescence image is very weak relative to the light in the visible light band for forming the subject image.

On the other hand, it was also suggested that in a light source device used when a subject was illuminated with illumination light including beams of light of the wavelength of excitation light and the fluorescent light wavelength longer than that so as to simultaneously observe both an observation image formed by weak fluorescent light emitted from the portion being observed in the subject and a subject image formed by reflected light from the subject, a white light source should be used to adjust the intensity of the illumination light component in the wavelength region longer than or equal to the fluorescent light wavelength, thereby balancing the quantity of light between the fluorescence image and the background portion (Patent Literature 3). However, it is impossible for this light source device to balance the quantity of light between the fluorescence image and the subject image in the visible light band.

Furthermore, it was also suggested that in an endoscope for observing a fluorescence image in the infrared band and a subject image in the visible light band, a light source device using a white light source was provided with a band limiting rotary filter having a visible light transmitting filter and an infrared light transmitting filter which were disposed so as to divide a circular shape into two parts so that the filter regions to be used were changed for observing fluorescent light and for observing ordinary light, and to simultaneously observe the fluorescent light and the ordinary light, the band limiting rotary filter should be rotated, and an RGB rotating filter on the receiving side should also be rotated in synchronization therewith (Patent Literature 4). However, the band limiting rotary filter cannot change the ratio of the quantity of light between the excitation light for forming the fluorescence subject image and the light in the visible light band for forming the subject image. Furthermore, to simultaneously observe the fluorescence image and the subject image, the band limiting rotary filter of the light source device and the RGB filter of the light-receiving device have to be synchronized with each other, thus leading to the problem of the increased complexity of the whole system configuration.

Note that it is known to provide a light source for excitation light such as an infrared laser separately from a light source for illumination light in order to balance between the excitation light for forming a fluorescence image and light in the visible light band for forming a subject image. However, this case will also lead to an increase in the complexity of the whole system configuration.

CITATION LIST

Patent Literature

Patent Literature 1: Japanese Patent Application Laid-Open Publication No. 2001-78205

Patent Literature 2: Japanese Patent Application Laid-Open Publication No. 2008-188196

Patent Literature 3: Japanese Patent Application Laid-Open Publication No. 2008-259591

Patent Literature 4: Japanese Patent Application Laid-Open Publication No. Hei. 10-201707

SUMMARY OF INVENTION

Technical Problem

As described above, an object of the present invention is to enable a light source device to adjust, in a simple method, the quantity of light in the visible light region for forming a subject image and the quantity of excitation light in the infrared region for forming a fluorescence image so as not to allow the fluorescence image to be buried in the subject image when the subject image in the visible light region formed by reflected illumination light and the weak fluorescence image from a fluorescent substance in the subject are simultaneously observed.

Solution to Problem

The present inventors have found that the aforementioned problems could be solved by using, in an illumination optical system, an aperture diaphragm which functions as an aperture diaphragm for light in the wavelength region of illumination light for forming the subject image and which transmits light in the wavelength region of excitation light for forming the fluorescence image without stopping it.

That is, the present invention provides, as a first aperture diaphragm, an illumination aperture diaphragm to be used in a light source device when a subject image formed by reflected illumination light in a visible light region and the fluorescence image from fluorescent substance in a subject are simultaneously observed, the illumination aperture diaphragm including an annular filter region formed on a base material and an aperture region formed inside the filter region, the filter region serving to transmit light in a wavelength region of excitation light for allowing the subject to emit fluorescent light and serving to reduce or block the transmission of light in a visible light region for forming the subject image.

The present invention provides, as a second aperture diaphragm, an illumination aperture diaphragm to be used in a light source device when a subject image formed by reflected illumination light in a visible light region and a fluorescence image from a fluorescent substance in a subject are simultaneously observed, the illumination aperture diaphragm including a plurality of diaphragm blade members, on which a filter portion is partially or entirely formed, and having a filter region which is formed of the filter portions of the plurality of diaphragm blade members and an aperture region located inside the filter region, the filter region serving to transmit light in a wavelength region of excitation light for allowing the subject to emit fluorescent light and serving to reduce or block the transmission of light in a visible light region for forming the subject image.

Furthermore, the present invention provides a light source device to be used for an imaging device for simultaneously observing a subject image formed by illumination light and a fluorescence image from a portion of a subject being observed, the light source device including a white light source and the aforementioned illumination aperture diaphragm. More particularly, the present invention provides a light source device which is used for an endoscope device.

Advantageous Effects of Invention

According to the first and second illumination aperture diaphragms of the present invention, there is formed an aperture region inside a filter region which transmits light in the wavelength region of excitation light for allowing a portion of a subject being observed to emit fluorescent light and which reduces or blocks the transmission of light in a visible light region for forming a subject image. Thus, only the light in the visible light region for forming the subject image is reduced without reducing the light in the wavelength region of the excitation light which passes through the filter region and the aperture region. Thus, when the aperture diaphragm is used in a light source device, it is possible, in a simple system configuration using a white light source, to improve the ratio between the quantity of light of the fluorescence image and the quantity of light of the subject image and prevent the fluorescence image from being buried in the subject image.

Furthermore, according to the second illumination aperture diaphragm of the present invention, the area of the aperture region is variable. Thus, when this aperture diaphragm is used in a light source device, it is possible, in a simple system configuration, to balance the quantities of light of the fluorescence image and the subject image in a more appropriate manner.

DESCRIPTION OF EMBODIMENTS

Figure 1:
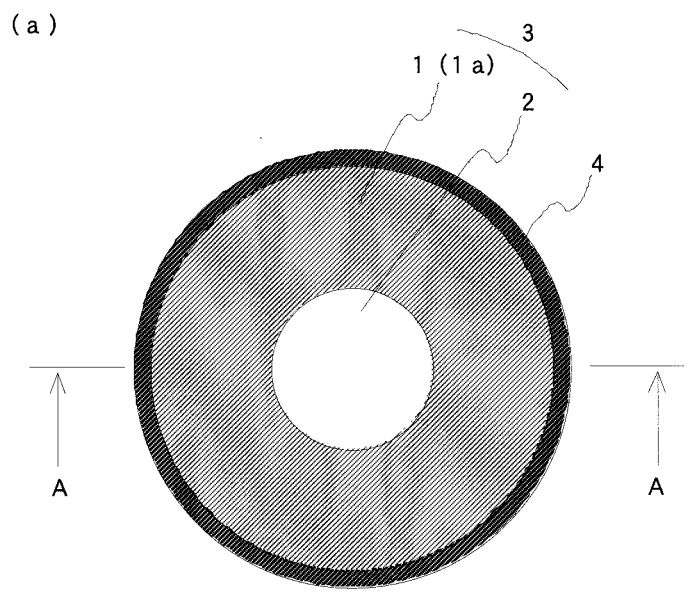
FIG. 1 includes a plan view and a cross-sectional view illustrating a doughnut-shaped aperture diaphragm 100A according to an embodiment of the present invention.
Figure 1:
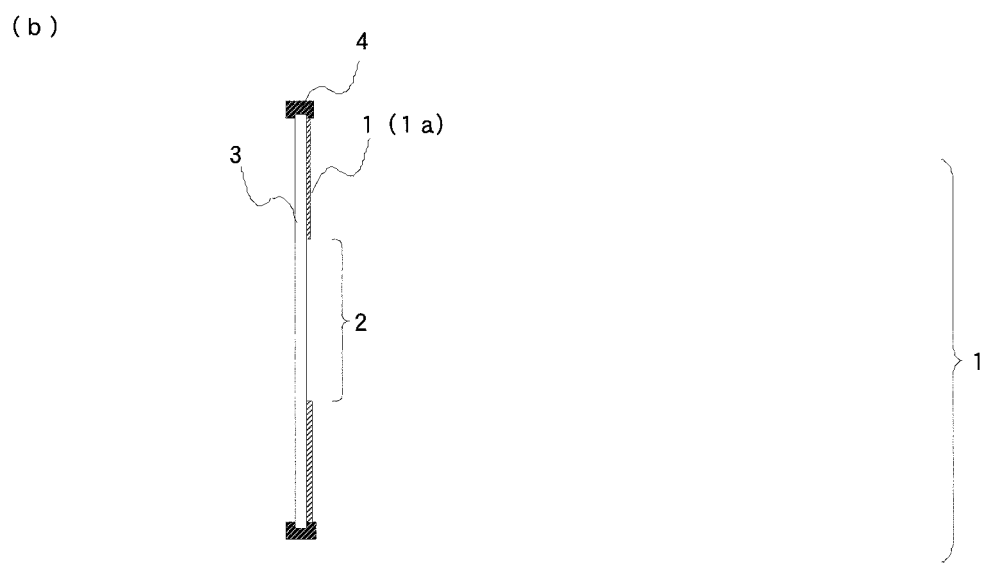

Now, the present invention will be described in more detail below with reference to the drawings. Note that the same reference characters refer to the same or equivalent elements in all the drawings.

FIG. 1 includes a plan view (FIG. 1(a)) and a cross-sectional view (FIG. 1(b)) taken along A-A illustrating a doughnut-shaped aperture diaphragm 100A which is an embodiment of a first illumination aperture diaphragm according to the present invention. The doughnut-shaped aperture diaphragm 100A is made up of a flat plate-like base material 3, which has an annular filter region 1 and a circular aperture region 2 formed inside the filter region 1, and an outer frame 4 fitted over the outer periphery of the flat plate-like base material 3. More specifically, the filter region 1 has a filter layer 1a which is annularly provided on a surface of the circular, transparent, flat, plate-like base material 3, and the center region of the flat plate-like base material 3 on which no filter layer is formed serves as the aperture region 2.

The aperture diaphragm 100A is constructed for use with an illumination optical system, in which the filter region 1 transmits light in the wavelength region of excitation light for allowing a subject to emit fluorescent light substantially without attenuation, and reduces or blocks light in the visible light region for forming a subject image. Note that when the wavelength region of the excitation light for allowing the subject to emit fluorescent light overlaps the wavelength region of the visible light for forming the subject image, the filter region 1 transmits light in the wavelength region of the excitation light substantially without attenuation and reduces or blocks the light which is in the visible light region for forming the subject image and outside the wavelength region of the excitation light.

Furthermore, the aperture region 2 transmits, substantially without attenuation, light in the wavelength region of the excitation light for allowing the subject to emit fluorescent light and light in the visible light region (for example, of wavelengths from 400 to 800 nm) for forming the subject image. This aperture region 2 may also be such a region that has no filtering function for a particular wavelength region and fully transmits any beams of light. Note that this embodiment employs the circular aperture region 2. However, in the present invention, the aperture region 2 can take various types of shape, for example, elliptical or rectangular shapes.

Here, the light transmission property of the filter region 1 can be appropriately determined depending on the type of subjects to be observed, light-sensitive substances, and light contrast agents, and the purpose of the observations. For example, suppose that the ICG is accumulated in the living body to employ the accumulated portion as a portion to be observed, so that the ICG is irradiated with excitation light to emit fluorescent light, and the fluorescent light is observed. In this case, since the peak of the excitation wavelength of the ICG is at 805 nm and the peak of the fluorescent light wavelength of the ICG is at 845 nm, employed as the excitation wavelength region is a band from 750 to 810 nm, and white light including light in the excitation wavelength region is preferably employed as the light source. Thus, the filter region 1 is configured to transmit light in the excitation wavelength region from 750 to 810 nm, but to reduce or block light having a shorter wavelength than that in the visible light region.

Figure 2:
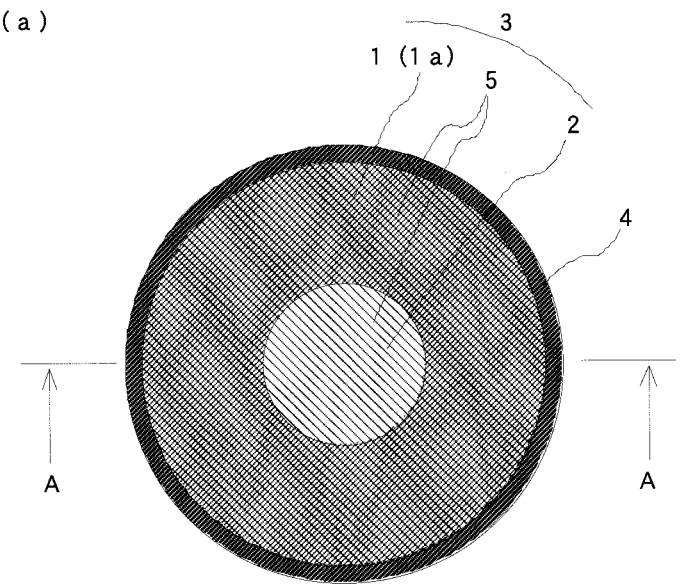
FIG. 2 includes a plan view and a cross-sectional view illustrating a doughnut-shaped aperture diaphragm 100B according to an embodiment of the present invention.
Figure 2:
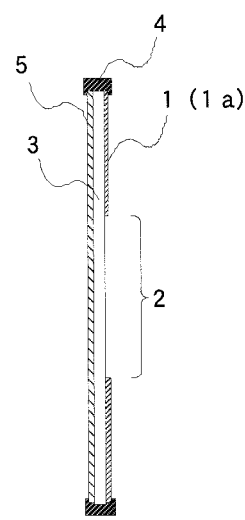

Note that setting the light transmission property of the doughnut-shaped aperture diaphragm 100A in this manner allows light in the fluorescent wavelength region to pass through the aperture region 2. Thus, when the doughnut-shaped aperture diaphragm 100A is used, it is preferable to employ a fluorescent wavelength region cutoff filter for blocking light having a longer wavelength than 810 nm. Or alternatively, like a doughnut-shaped aperture diaphragm 100B shown in FIG. 2, the filter region 1 may be annularly formed on one surface of the flat plate-like base material 3, and a fluorescent wavelength region cutoff filter layer 5 that blocks light having a longer wavelength than 810 nm may be formed on the other entire surface of the flat plate-like base material 3.

On the other hand, when a hematoporphyrin derivative (HpD) is used as a light-sensitive substance in the PDD method, excitation light having a peak wavelength at 405 nm causes a tumor cell having HpD accumulated therein to emit fluorescent light at peak wavelengths of 630 nm and 690 nm. In response thereto, it is preferable that the wavelength region of the excitation light is set to 385 to 425 nm, the wavelength region of the fluorescent light to be observed is set to 610 to 720 nm, and the light source employed is white light including light in the wavelength region of the excitation light. Thus, the filter region 1 is preferably configured to transmit light at 385 to 425 nm, i.e., in the wavelength region of the excitation light, but block or reduce visible light having a shorter wavelength or visible light having a longer wavelength than light in that wavelength region. More preferably, the filter region 1 is configured to block light having a shorter wavelength and having a longer wavelength than light in the wavelength region of the excitation light. On the other hand, as in the case of taking an observation image formed with the aforementioned ICG, it is preferable to use, as appropriate, the fluorescent wavelength region cutoff filter when the doughnut-shaped aperture diaphragm is used, or to provide the doughnut-shaped aperture diaphragm with the fluorescent wavelength region cutoff filter layer.

The ratio between the area (S1) of the filter region 1 and the area (S2) of the aperture region 2 is determined, as appropriate, depending on the intensity of the light source or the sensitivity of the imaging device so that an observation image formed with fluorescent light from a portion of the subject being observed can be clearly observed without being buried in a subject image formed with illumination light.

The filter layer 1a which forms the filter region 1 can be formed into the flat plate-like base material 3 by a typical thin film deposition method for optical filters such as by vapor deposition or by sputtering so as to have the aforementioned light transmission property.

In this embodiment, the flat plate-like base material 3 is preferably formed using a transparent parallel flat plate, and can be formed, for example, of blue plate glass, white plate glass, optical glass, or acrylic resin plate. The thickness of the flat plate-like base material 3 can be determined, as appropriate, depending on the material of the flat plate-like base material 3 and the outer diameter of the filter region 1.

Figure 3:
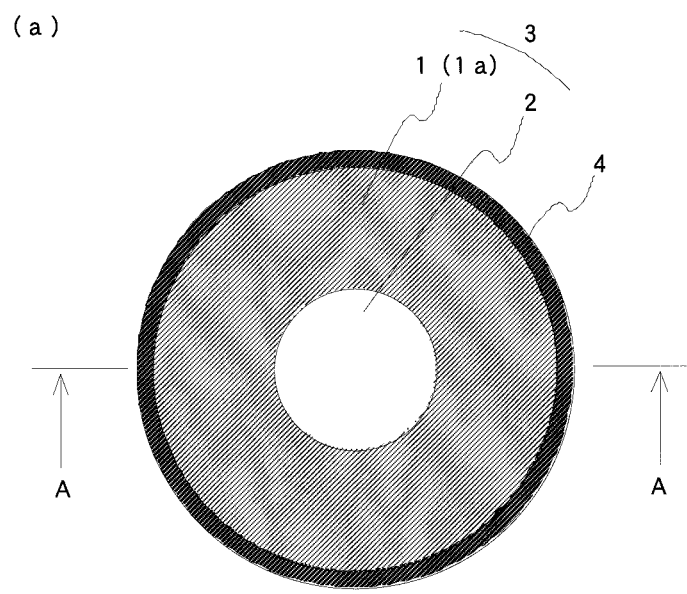
FIG. 3 includes a plan view and a cross-sectional view illustrating a doughnut-shaped aperture diaphragm 100C according to an embodiment of the present invention.
Figure 3:
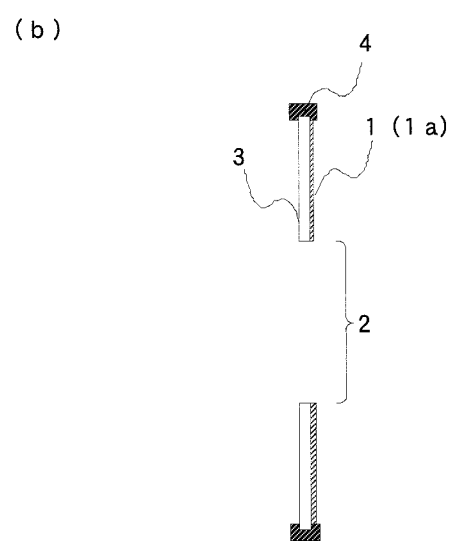
Figure 4:
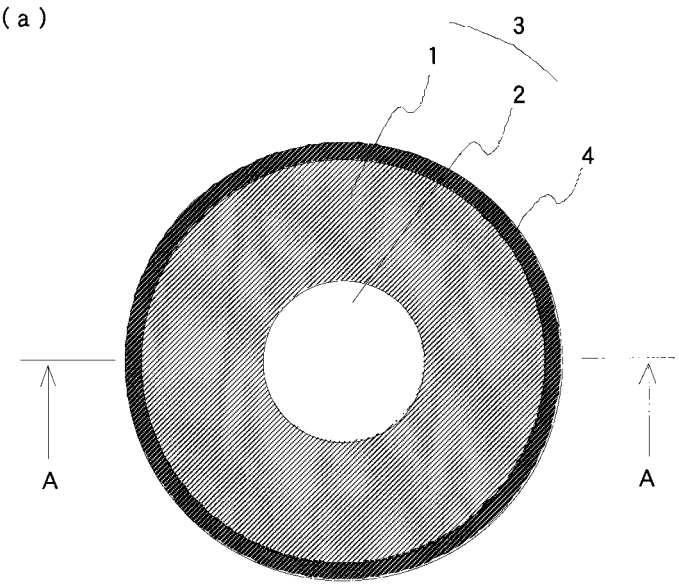
FIG. 4 includes a plan view and a cross-sectional view illustrating a doughnut-shaped aperture diaphragm 100D according to an embodiment of the present invention.
Figure 4:
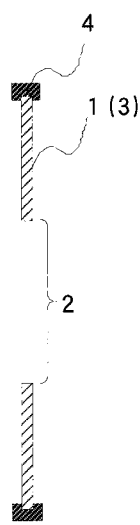

The aperture diaphragm of the present invention can take various forms. For example, like an aperture diaphragm 100C shown in FIG. 3, the flat plate-like base material 3 to be employed can be an annular base plate with the aperture region 2 cut away. Or alternatively, like an aperture diaphragm 100D shown in FIG. 4, the filter region 1 may be formed of a flat plate-like base material 3 with color material uniformly dispersed therein, and the flat plate-like base material 3 itself may be cut off to thereby form the aperture region 2.

Figure 5:
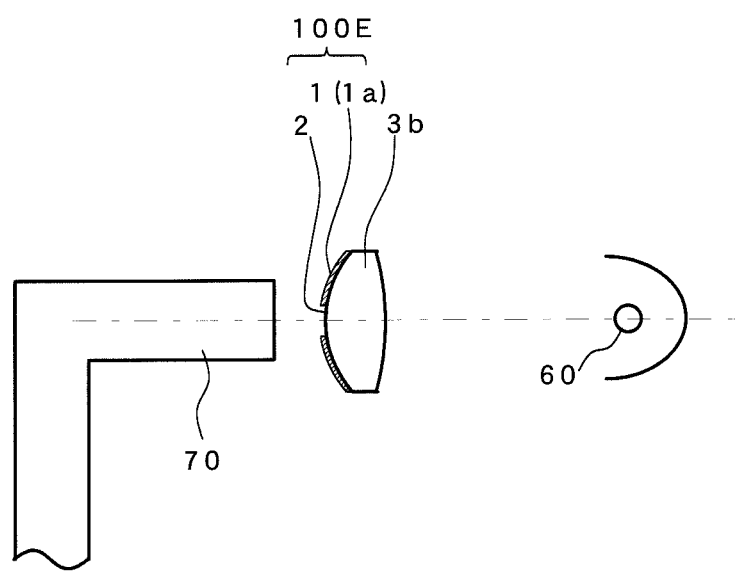
FIG. 5 is a cross-sectional view illustrating a lens system in which a doughnut-shaped aperture diaphragm 100E according to an embodiment of the present invention is incorporated.

On the other hand, the filter layer 1a forming the filter region 1 is not necessarily formed on the flat plate-like base material 3. The base material on which the filter layer 1a is to be formed may be a lens, and the filter layer 1a is formed on the surface thereof. FIG. 5 shows an aperture diaphragm 100E in which the filter layer 1a is annularly formed on a surface of a condenser lens 3b for condensing light emitted by a light source 60 into a light guide fiber 70 of an endoscope.

Forming the filter layer 1a on the surface of a lens reduces the space occupied by the aperture diaphragm when compared with an aperture diaphragm having the filter layer provided on the base material as an independent optical member. Note that the lens 3b on which the filter layer 1a is formed may preferably be located in the vicinity of a position at which the aperture diaphragm is disposed in a lens system inside a conventional light source device.

Figure 6:
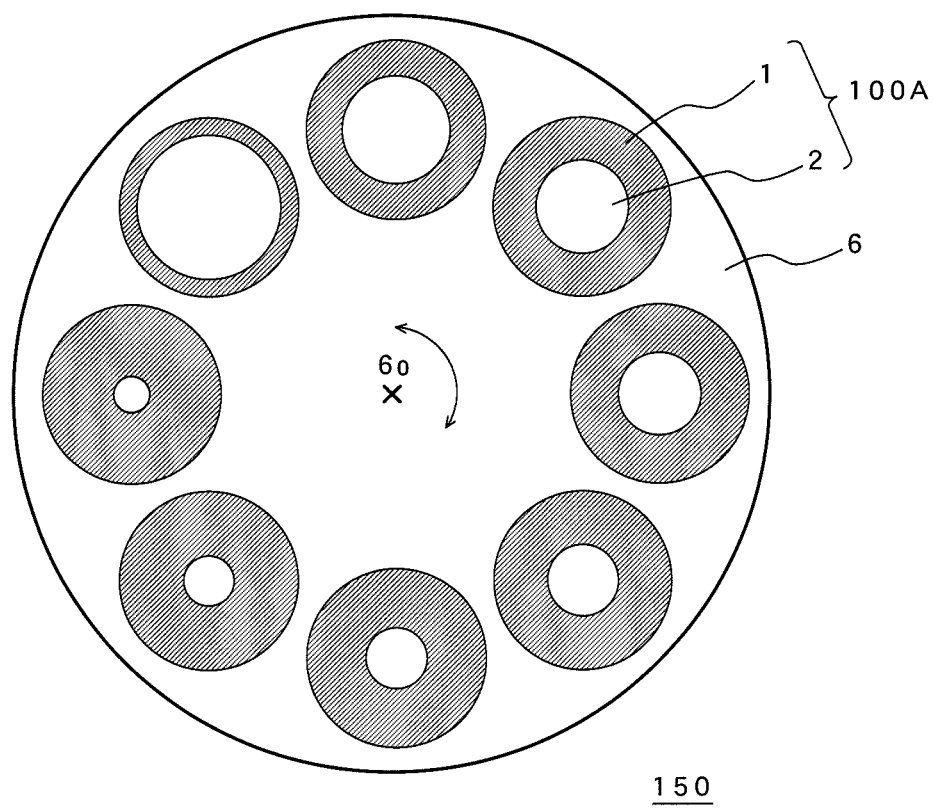
FIG. 6 is a plan view illustrating a rotary aperture diaphragm 150 into which a plurality of doughnut-shaped aperture diaphragms 100A are combined.

FIG. 6 is a plan view illustrating a rotary aperture diaphragm 150 in which a plurality of aperture diaphragms, which are similar to the aforementioned doughnut-shaped aperture diaphragm 100A and have different area ratios between the filter region 1 and the aperture region 2, are disposed around the center of rotation 6o of a disc-shaped base plate 6. According to the rotary aperture diaphragm 150, the disc-shaped base plate 6 can be rotated as indicated by the arrow, so that a doughnut-shaped aperture diaphragm 100A which has a desired ratio between the filter region 1 and the aperture region 2 can be easily chosen for illuminating the subject.

Figure 7:
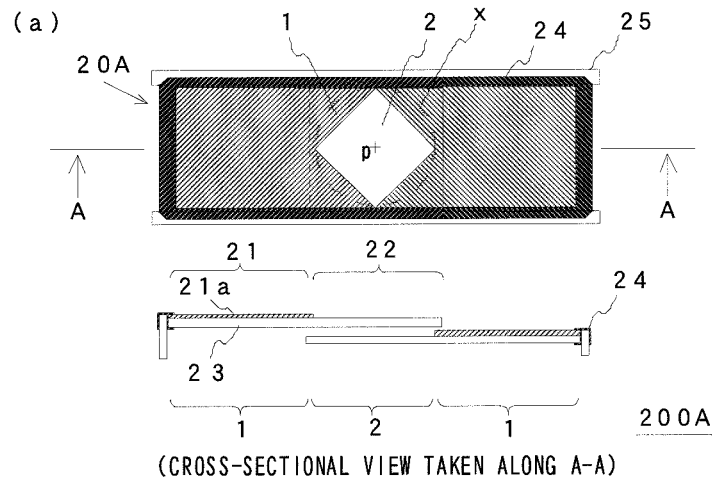
FIG. 7 includes plan views and cross-sectional views for explaining the operation of a two-blade-type aperture diaphragm 200A according to an embodiment of the present invention.
Figure 7:
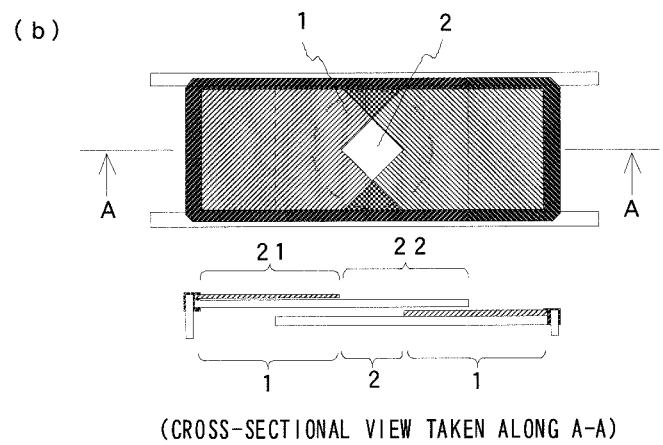
Figure 7:
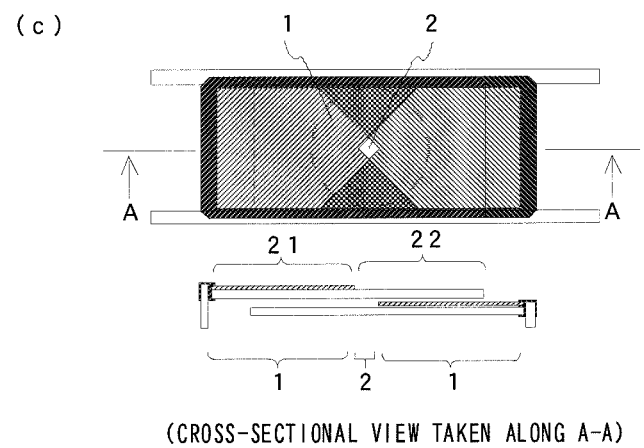
Figure 8:
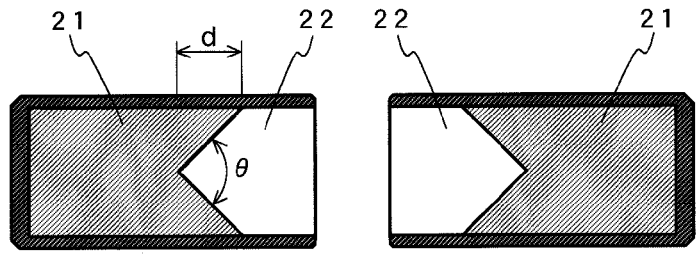
FIG. 8 is a plan view illustrating a diaphragm blade member 20A which constitutes a two-blade-type aperture diaphragm 200A according to an embodiment of the present invention.

FIG. 7 includes explanatory views illustrating a two-blade-type aperture diaphragm 200A which is an embodiment of a second diaphragm of the present invention, and FIG. 8 is a plan view illustrating a pair of diaphragm blade members 20A which constitute the two-blade-type aperture diaphragm 200A.

The diaphragm blade members 20A each have a filter portion 21 on which a filter layer 21a is formed on the right or left side of a surface of a rectangular flat plate-like base material 23 and a non-filter portion 22 on which no filter layer 21a is formed. The diaphragm blade members 20A are fitted into an outer frame 24. Here, the filter layer 21a has a V-shaped recess opened toward the non-filter portion 22. Like the filter layer 1a of the aforementioned doughnut-shaped aperture diaphragm 100A, the filter layer 21a has the light transmission property of transmitting, substantially without attenuation, light in the wavelength region of excitation light for allowing a subject to emit fluorescent light and reducing or blocking light in the visible light region for forming a subject image. The filter layer 21a is formed, for example, by vapor deposition of thin film like the filter layer 1a of the aforementioned doughnut-shaped aperture diaphragm 100A. On the other hand, as with the aforementioned aperture diaphragm 100A, the rectangular flat plate-like base material 23 is formed, for example, of a transparent glass plate or an acrylic resin plate.

The two-blade-type aperture diaphragm 200A shown in FIG. 7 is formed in a manner such that a pair of diaphragm blade members 20A are combined so that both the non-filter portions 21 overlap with each other and then movably mounted to a rail 25. According to the two-blade-type aperture diaphragm 200A, the overlapping region of the non-filter portions 22 of the pair of the diaphragm blade members 20A serves as the aperture region 2 of the two-blade-type aperture diaphragm 200A so as to transmit the light in the wavelength region of excitation light for allowing the subject to emit fluorescent light and the light in the visible light region for forming the subject image. On the other hand, a pair of filter portions 21 surrounding the aperture region 2 serve as the filter region 1 of the two-blade-type aperture diaphragm 200A so as to allow the transmission of light in the wavelength region of the excitation light for allowing the subject to emit fluorescent light and reduce or block visible light for forming the subject image.

Thus, according to the two-blade-type aperture diaphragm 200A, the area of the aperture region 2 can be varied. For example, the area of the aperture region 2 can be continuously changed into the state in which the aperture region 2 is maximized as shown in FIG. 7(a), the state in which the aperture region 2 is reduced as shown in FIG. 7(b), and the state in which the aperture region 2 is further reduced as shown in FIG. 7(c). It is thus possible to balance, as appropriate, between the quantities of the light for forming the subject image and the excitation light for forming the fluorescence image. Note that in FIG. 7, the broken line circle X around the aperture region 2 indicates the diameter of an optical path from a light source at a position at which the two-blade-type aperture diaphragm 200A is attached to the optical system of a light source device or the like. As such, irrespective of the aperture region 2 being closed or opened, the diameter of the filter region 1 is preferably made greater than the diameter of the optical path from the light source at the position of installation of the two-blade-type aperture diaphragm 200A so that the filter region 1 does not block the optical path from the light source. This makes it possible to reduce a loss in the excitation light component contained in the light source.

Furthermore, to combine a pair of diaphragm blade members 20A so that both the non-filter portions 22 overlap with each other in the two-blade-type aperture diaphragm 200A, it is desirable to dispose the pair of diaphragm blade members 20A as close to each other as possible so long as the opposing surfaces thereof are not in contact with each other.

As a drive mechanism for the diaphragm blade members 20A, the pair of diaphragm blade members 20A are preferably connected to each other using a well-known connector in a manner such that the pair of diaphragm blade members 20A are displaced in right and left symmetry with respect to the center p of the aperture region 2. Furthermore, the diaphragm blade members 20A may be driven manually or by a stepping motor as the driving source.

The aperture diaphragm of the present invention can also take other various forms. For example, in the diaphragm blade members 20A shown in FIG. 8, the opening angle θ of the V shape of the filter portion 21 or the depth d of the V shape is not limited to a particular one so long as the pair of non-filter portions 22 can be overlapped to thereby form the aperture region 2.

Figure 9:
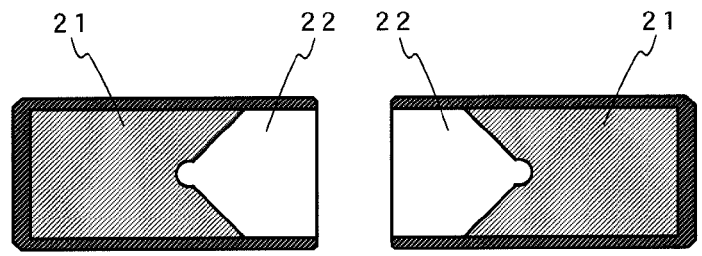
FIG. 9 is a plan view illustrating a diaphragm blade member 20B which constitutes a two-blade-type aperture diaphragm according to an embodiment of the present invention.
Figure 10:
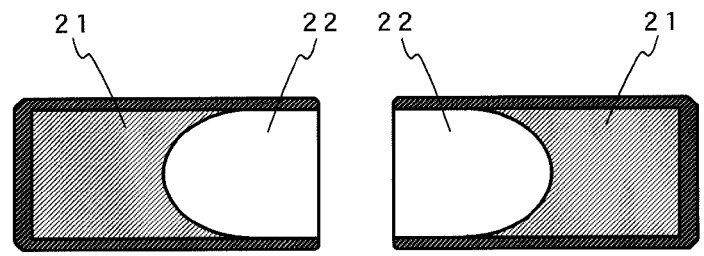
FIG. 10 is a plan view illustrating a diaphragm blade member 20C which constitutes a two-blade-type aperture diaphragm according to an embodiment of the present invention.

In the diaphragm blade members 20A shown in FIG. 8, the filter portion 21 has a V-shaped recess opened toward the non-filter portion 22. However, the shape of the recess itself is not limited to a particular one so long as the pair of non-filter portions 22 can be overlapped with each other to form the aperture region 2. Thus, like a diaphragm blade member 20B shown in FIG. 9, the tip of the V-shaped recess may be recessed in a semi-circular shape so that the aperture region 2 forms a circle when the area of the aperture region 2 is minimized. Furthermore, like a diaphragm blade member 20C shown in FIG. 10, the filter portion 21 may have a semi-elliptical recess opened toward the non-filter portion 22.

Figure 11:
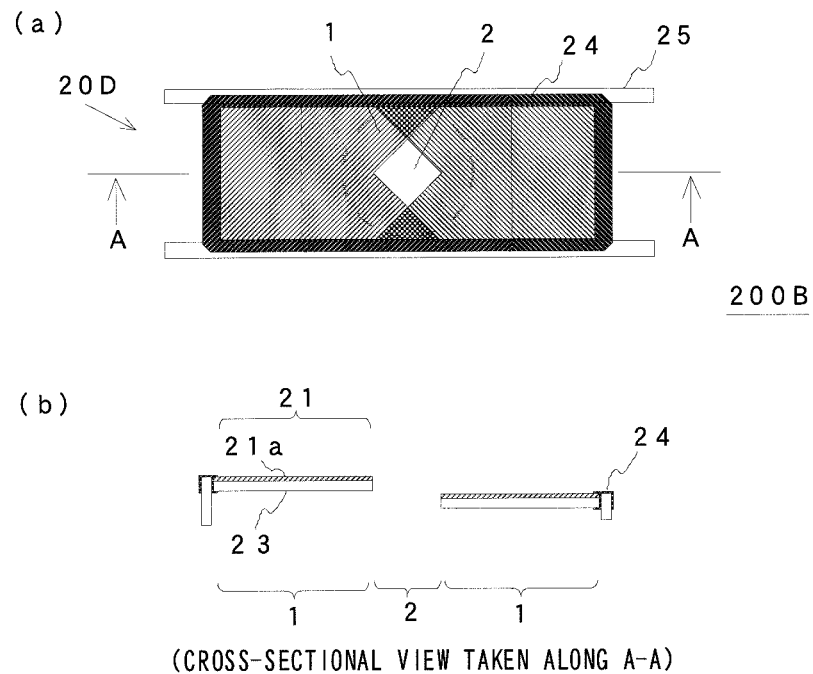
FIG. 11 includes a plan view and a cross-sectional view illustrating a two-blade-type aperture diaphragm 200B according to an embodiment of the present invention.
Figure 12:
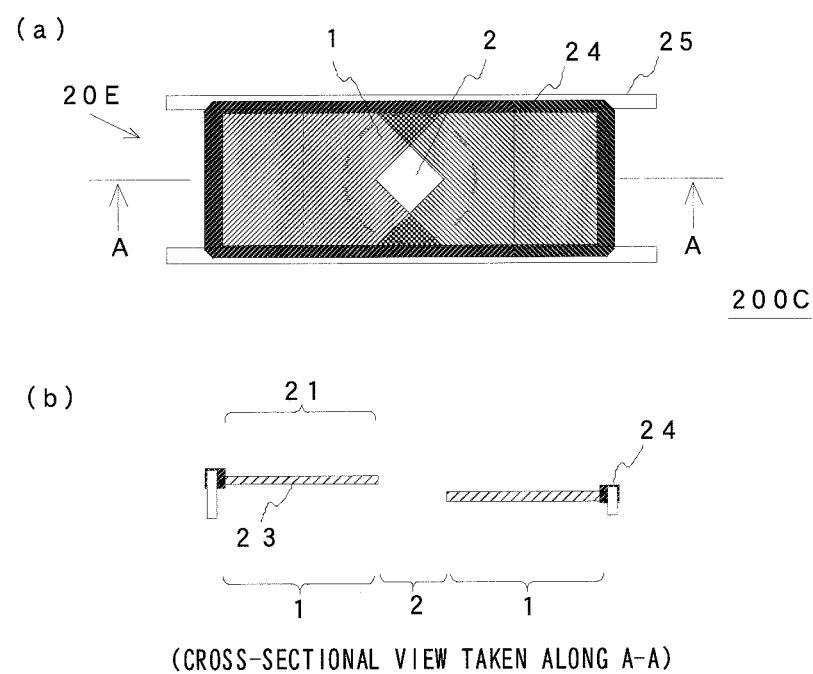
FIG. 12 includes a plan view and a cross-sectional view illustrating a two-blade-type aperture diaphragm 200C according to an embodiment of the present invention.

Like a two-blade-type aperture diaphragm 200B shown in FIG. 11, the planar shape itself of the flat plate-like base material 23 on which a diaphragm blade member 20D is formed is shaped so as to have a recess in the same manner as the filter portions 21 do. Or alternatively, like a two-blade-type aperture diaphragm 200C shown in FIG. 12, the flat plate-like base material 23 which has color material uniformly dispersed therein and which itself thus has the same light transmission property as that of the filter layer 21a may be used and be cut into a shape having the recess, thereby forming the aperture region 2.

Figure 13:
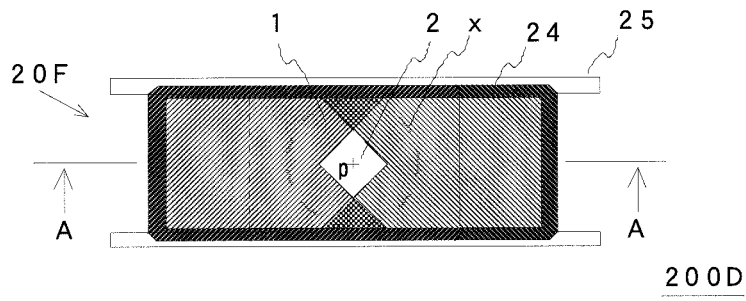
FIG. 13 includes a plan view and a cross-sectional view illustrating a two-blade-type aperture diaphragm 200D according to an embodiment of the present invention.
Figure 13:
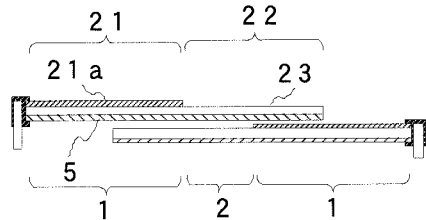

Furthermore, like the aforementioned doughnut-shaped aperture diaphragm, the aforementioned two-blade-type aperture diaphragm of the present invention may be configured in a manner such that as shown in FIG. 13, the fluorescent wavelength region cutoff filter layer 5 may be provided, as required, on the flat plate-like base material 23 opposite to the filter layer 21a.

The aperture diaphragm of the present invention can also take other various forms. For example, three or more diaphragm blade members having a filter portion and a non-filter portion may be combined to form a filter region and an aperture region located inside the filter region. However, an excessive overlap between the filter portions may cause the filter portions to be thermally expanded due to heat from the light source and thereby produce strain in the overlap of the filter portions, resulting in nonuniform illumination. Thus, it is preferable to employ the two-blade-type aperture diaphragm rather than an aperture diaphragm having three or more diaphragm blade members from the viewpoint of reducing the tendency to cause nonuniform illumination.

The aperture diaphragm of the present invention can be used with the light source device for a wide variety of types of imaging devices which simultaneously take a subject image formed by illumination light and a fluorescence image from a portion of the subject being observed, thereby preventing the fluorescence image from being weakened relative to the subject image.

Figure 14:
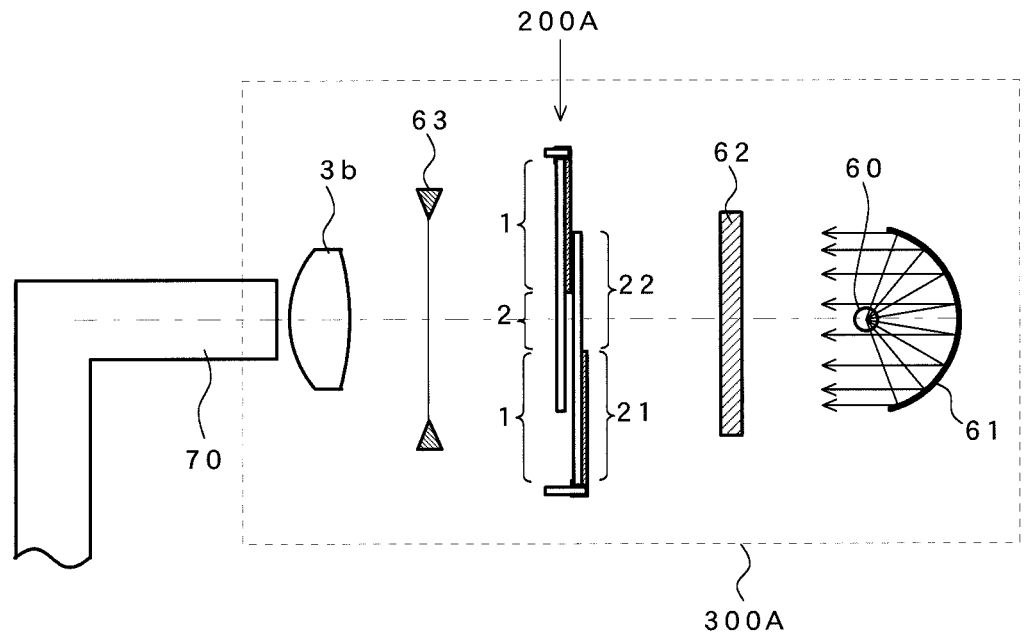
FIG. 14 is a schematic diagram of a light source device 300A according to an embodiment of the present invention.

FIG. 14 is a schematic diagram illustrating the two-blade-type aperture diaphragm 200A of the present invention which is incorporated into a light source device 300A for a well-known near-infrared fluorescence image capturing endoscope device using the ICG. The endoscope device to which the light source device 300A is attached takes simultaneously an image of a living-body subject formed by visible light and a fluorescence image in the band of infrared light that is emitted by the ICG given to the living tissue. The endoscope device can be configured in the same manner as the endoscope device disclosed in Patent Literature 4 or the endoscope device disclosed in PCT/JP2009/67352. Preferably, like the endoscope device disclosed in PCT/JP2009/67352, an endoscope device to be used has an aperture diaphragm in front of an imaging device such as CCDs, the aperture diaphragm being configured to transmit light in the wavelength region corresponding to that of the fluorescent light from a portion of the subject being observed and to reduce or block the transmission of light in the visible light region for forming the subject image. This can provide a further improved ratio of the strength of the fluorescence image to that of the subject image in a simplified structure.

The light source device 300A has: a white light source 60 such as a halogen lamp, xenon lamp, or LED; a concave mirror 61 provided behind the white light source 60; and a fluorescent wavelength region cutoff filter 62, the two-blade-type aperture diaphragm 200A shown in FIG. 7, and the condenser lens 3b, which are sequentially disposed in front of the white light source 60. Furthermore, between the two-blade-type aperture diaphragm 200A and the condenser lens 3b, it is possible to provide, as required, a total light quantity diaphragm 63 for reducing the total quantity of illumination light.

According to the light source device 300A, the ratio between the filter region 1 of the two-blade-type aperture diaphragm 200A and the aperture region 2 can be adjusted. This adjustment makes it possible to supply illumination light having an appropriate ratio between the quantities of excitation light and light in the visible light region to the light guide fiber 70 of the endoscope device.

Note that in such a light source device 300A, the aforementioned other two-blade-type aperture diaphragms 200B to 200D, the doughnut-shaped aperture diaphragms 100A to 100E, or the rotary aperture diaphragm 150 may also be provided in place of the two-blade-type aperture diaphragm 200A shown in FIG. 7.

INDUSTRIAL APPLICABILITY

The aperture diaphragm of the present invention is useful for a light source device in a fluorescent imaging device using a fluorescent light reagent such as the ICG and in a medical imaging device such as for the PDD and PDT, and a light source device to be employed to take a fluorescence image in the analytical test of food or various materials.

REFERENCE SIGNS LIST

1 filter region
1a filter layer
2 aperture region
3 flat plate-like base material
3b condenser lens
4 outer frame
5 fluorescent wavelength region cutoff filter layer
6 disc-shaped base plate
20A, 20B, 20C, 20D, 20E, 20F diaphragm blade member
21 filter portion
21a filter layer
22 non-filter portion
23 flat plate-like base material
24 outer frame
25 rail
50 excitation light cutoff filter
60 light source
61 concave mirror
62 fluorescent wavelength region cutoff filter
63 total light quantity diaphragm
70 light guide fiber
100A, 100B, 100C, 100D, 100E doughnut-shaped aperture diaphragm
150 rotary aperture diaphragm
200A, 200B, 200C, 200D two-blade-type aperture diaphragm
300A light source device

The invention claimed is:

1. An illumination aperture diaphragm in a light source device for supplying illumination light to a subject for use when a subject image formed by reflected illumination light in a visible light region and a fluorescence image from fluorescent substance in a subject are simultaneously observed,
the illumination aperture diaphragm comprising an annular filter region formed on a base material and an aperture region formed inside the filter region, the filter region serving to transmit light in a wavelength region of excitation light for allowing the subject to emit fluorescent light and serving to reduce or block the transmission of light in a visible light region for forming the subject image.

2. The illumination aperture diaphragm according to claim 1, wherein the excitation light is infrared light.

3. The illumination aperture diaphragm according to claim 2, wherein the base material is flat, plate-like with the annular filter region formed on one surface of the base material and with the other surface of the base material being provided entirely with a filter layer which blocks the transmission of light in the wavelength region of the fluorescent light.

4. A light source device to be used for an imaging device for simultaneously observing a subject image formed by illumination light and a fluorescence image from a portion of a subject being observed, the light source device comprising a white light source and the illumination aperture diaphragm according to claim 1.

5. The light source device according to claim 4, wherein the light source device is used for an endoscope device.

6. The illumination aperture diaphragm according to claim 1, wherein the aperture diaphragm has a surface provided entirely with a filter layer which blocks the transmission of light in the wavelength region of the fluorescent light.

7. An illumination aperture diaphragm to be used in a light source device when a subject image formed by reflected illumination light in a visible light region and a fluorescence image from a fluorescent substance in a subject are simultaneously observed, the illumination aperture diaphragm comprising a plurality of diaphragm blade members each having a surface partially or entirely formed with a filter portion, and having a filter region which is formed of the filter portions of the plurality of diaphragm blade members and an aperture region located inside the filter region, the filter region serving to transmit light in a wavelength region of excitation light for allowing the subject to emit fluorescent light and serving to reduce or block the transmission of light in a visible light region for forming the subject image.

8. The illumination aperture diaphragm according to claim 7, wherein the aperture region has a variable area.

9. The illumination aperture diaphragm according to claim 8, wherein the excitation light is infrared light.

10. The illumination aperture diaphragm according to claim 9, wherein the filter region has a diameter greater than a diameter of an optical path from a light source, at a position at which the illumination aperture diaphragm is mounted, and the filter region does not block the optical path.

11. A light source device to be used for an imaging device for simultaneously observing a subject image formed by illumination light and a fluorescence image from a portion of a subject being observed, the light source device comprising a white light source and the illumination aperture diaphragm according to claim 7.

12. The light source device according to claim 11, wherein the light source device is used for an endoscope device.

13. The illumination aperture diaphragm according to claim 7, wherein the excitation light is infrared light.

14. The illumination aperture diaphragm according to claim 7, wherein the filter region has a diameter greater than a diameter of an optical path from a light source, at a position at which the illumination aperture diaphragm is mounted, and the filter region does not block the optical path.

\* \* \* \* \*